US012797517B2

United States Patent
(12) United States Patent
Rahimi et al.

(10) Patent No.: US 12,797,517 B2
(45) Date of Patent: Nov. 17, 2026

(54) OXYGEN-GENERATING MESH MATERIAL

(71) Applicant: Purdue Research Foundation, West Lafayette, IN (US)

(72) Inventors: Rahim Rahimi, West Lafayette, IN (US); Amin Zareei, Lafayette, IN (US); Ian B. Woodhouse, Manchester, MO (US)

(73) Assignee: Purdue Research Foundation, West Lafayette, IN (US)

(*) Notice: Subject to any disclaimer, the term of this patent is extended or adjusted under 35 U.S.C. 154(b) by 259 days.

(21) Appl. No.: 18/807,880

(22) Filed: Aug. 16, 2024

(65) Prior Publication Data

US 2024/0408281 A1 Dec. 12, 2024

Related U.S. Application Data

(62) Division of application No. 17/317,829, filed on May 11, 2021, now abandoned.

(Continued)

(51) Int. Cl.
*A61L 27/56* (2006.01)
*A61L 27/26* (2006.01)
(Continued)

(52) U.S. Cl.
CPC ............... *A61L 27/56* (2013.01); *A61L 27/26* (2013.01); *A61L 27/58* (2013.01); *C08G 63/08* (2013.01);
(Continued)

(58) Field of Classification Search
CPC .......... A61L 27/56; A61L 27/26; A61L 27/58; A61L 2400/18; A61L 2300/11; A61L 2300/404; A61L 31/06; A61L 31/148; A61L 31/16; A61L 31/146; C08G 63/08; C08G 2230/00; C08J 3/201; C08J 2367/04; C08J 5/18; C08K 3/22; C08K 2003/2206; C08L 75/04; C08L 67/04
See application file for complete search history.

(56) References Cited

U.S. PATENT DOCUMENTS

| | | | |
|---|---|---|---|
| 9,962,250 | B2 | 5/2018 | Priewe et al. |
| 10,493,040 | B2 | 12/2019 | Harrison et al. |
| 2008/0118550 | A1 | 5/2008 | Martakos et al. |

OTHER PUBLICATIONS

M. Zhang, "The Development of Oxygen-generating Materials and Cell Separation Techniques for Tissue Engineering," A Dissertation Submitted to the Faculty of University of Minnesota, published Aug. 2018, p. 1-168.*

(Continued)

*Primary Examiner* — Monica A Shin
(74) *Attorney, Agent, or Firm* — Purdue Research Foundation

(57) ABSTRACT

The present disclosure relates to a novel oxygen-generating biodegradable mesh material, and to methods of making and using the novel oxygen-generating biodegradable mesh material. More specifically, a novel surgical mesh has been developed, wherein the surgical mesh has a flexible basic structure and comprises a plurality of pores, wherein the surgical mesh has a first face and a second opposite face, wherein the surgical mesh is made of a substantially homogeneous material comprising a biodegradable polymeric material and an oxygen-generating material.

14 Claims, 5 Drawing Sheets

Related U.S. Application Data

(60) Provisional application No. 63/023,956, filed on May 13, 2020.

(51) Int. Cl.
*A61L 27/58* (2006.01)
*C08G 63/08* (2006.01)
*C08J 3/20* (2006.01)
*C08K 3/22* (2006.01)

(52) U.S. Cl.
CPC ................ *C08J 3/201* (2013.01); *C08K 3/22* (2013.01); *A61L 2400/18* (2013.01); *C08G 2230/00* (2013.01); *C08K 2003/2206* (2013.01)

(56) References Cited

OTHER PUBLICATIONS

J. Ko, "Melt electrospinning using Polycaprolactone (PCL) polymer for various applications: Experimental and Theoretical analysis," Copyright Junghyuk Ko, 2014, University of Victoria, p. 1-139.*

M. Stankovic et al., "Polymeric formulations for drug release prepared by hot melt extrusion: application and characterization," Drug Discovery Today, vol. 20, No. 7, Jul. 2015, p. 812-823.*

M. A. Repka et al., "Applications of Hot-Melt Extrusion for Drug Delivery," Expert Opin Drug Deliv. Dec. 2008; 5(12): 1357-1376. (Avaialble in PMC Feb. 21, 2018).*

Camci-Unal, G., et al., Oxygen Releasing Biomaterials for Tissue Engineering, Polym Int. Jun. 1, 2013; 62(6): 843-848.

Gholipourmalekabadi, M. et al., Oxygen-Generating Biomaterials: A New, Viable Paradigm for Tissue Engineering? Trends in Biotechnology, Dec. 2016, vol. 34, No. 12.

Baylón, K. et al., Past, Present and Future of Surgical Meshes:A Review, Membranes 2017, 7, 47.

Zhang, M., Dissertation, University of Minnesota, Aug. 2018 (Year: 2018).

Ashammaki et al., Biomacromolecules 2020, 21, 56-72, published Jul. 4, 2019 (Year: 2019).

* cited by examiner

OXYGEN-GENERATING MESH MATERIAL

CROSS-REFERENCE TO RELATED APPLICATIONS

This application is a divisional application of U.S. Utility application Ser. No. 17/317,829, filed on May 11, 2021, which is a utility application claiming the benefit of U.S. Provisional Patent Application No. 63/023,956, filed May 13, 2020. The entire disclosures of the above applications are incorporated herein by reference.

TECHNICAL FIELD

The present disclosure relates to an oxygen-generating mesh material, and to methods of making and using the oxygen-generating mesh material.

BACKGROUND

This section introduces aspects that may help facilitate a better understanding of the disclosure. Accordingly, these statements are to be read in this light and are not to be understood as admissions about what is or is not prior art.

Over 20 million hernia repairs are performed every year, costing the worldwide healthcare system over $94 billion. Surgical mesh is commonly used as a structural support for the affected tissue in hernia repair surgeries in addition to supplying a scaffold for tissue to grow into and form scar tissue, closing the hernia defect. Mesh is used in approximately 90% of inguinal hernia repairs, which account for about 75% of all hernia cases. While the use of mesh in hernia repair will decrease recurrence rate, there are some complications associated with the use of surgical mesh, including increased risk of infection, adhesion, and bowel obstruction. These complications may be due to the properties of the mesh being used, surgical conditions, or potentially prolonged hypoxic conditions slowing the rate of healing.

Researchers have developed many different types of meshes in order to find the "ideal" surgical mesh, which provides adequate long-term tensile strength, flexibility, biocompatibility, and proper integration into the tissue. These meshes can be broadly placed into two categories: resorbable and non-resorbable. Non-resorbable polymeric meshes, most commonly made from polypropylene, have a very low recurrence rate, but remain in the body permanently and are more likely to cause chronic pain, limited flexibility at the surgical site, and can erode into the surrounding tissue.

Resorbable meshes that are currently available do not maintain the minimum tensile strength of 24 kPa for the time needed for the surgical site to heal completely. Due to the lack of sustained structural support, a higher recurrence rate is reported for these resorbable meshes. In addition to higher recurrence rates, resorbable meshes are sometimes made of biological material which can be up to 100 times more expensive than synthetic, non-resorbable meshes. These biological meshes are derived from decellularized tissue to form collagen scaffolds created from porcine, human or bovine sources. Biological meshes don't trigger foreign body responses and provide better integration into the host tissue, but due to higher recurrence rates and higher costs, the commercial impact of these meshes is limited. A synthetic resorbable mesh with a longer life span would be advantageous as it would allow for unique processing methods and utilize higher performance materials such as resorbable polymers or composites to create a product that would not permanently remain in the body as a foreign object and still provides the required structural support.

Synthetic mesh has historically been made through one of the few processing methods: knitting, weaving, or expanded polymeric networks. Woven meshes require tightly packed filaments in order to avoid shifting of filaments and as such are largely not used in clinical applications. Knitting leads to a generally more flexible material, but it is generally weaker and also has a high variability of mechanical properties depending on the direction of applied stress. Expanded polymeric networks utilize a network of extremely fine interconnected fibers to form a sheet but can create pores too small for white blood cells. Bacteria are typically smaller than white blood cells; therefore, if pores are too small for white blood cells, bacteria would be able to proliferate in the pores and potentially lead to an infection.

Previous studies have investigated the potential to alleviate the risks associated with infection, adhesion to the surgical site, and prevent foreign body reactions to the mesh by coating the meshes with antibacterial materials (i.e. silver nanoparticles) or with a variety of other materials including collagen and omega-3 fatty acids. While these coatings are shown to prevent some of the aforementioned complications, most of the previous works have focused on coating of non-resorbable materials, hence they have the drawbacks of permanently remaining in the body, causing chronic pain, and limited flexibility.

When the surgical mesh is implanted into the body during a surgical procedure, the vascular structure of tissue is interrupted. The vascular system is responsible for bringing oxygen and other nutrients throughout the body, therefore when it is damaged, it limits the amount of nutrients locally available in the body. When normal oxygen levels are not present in the body, the area can progress to ischemic conditions that result in cell death and slowing down the healing of the wound. Therefore, many researchers have conducted studies to develop methods of generating oxygen locally in a wound to aid in the healing process. A common strategy to generate oxygen is through an implantable device that generates oxygen through electrolysis or chemical reactions. While electrolytic devices are able to produce oxygen for extended periods of time, they often require electronic components that remain in the body permanently or generate harmful compounds, such as chlorine, as byproducts. Oxygen generating compounds, however, are able to generate oxygen over the required timeframe while being absorbed into the body and avoiding harmful byproducts.

Therefore, there is an unmet need for a novel and economic surgical mesh that may address the issues.

SUMMARY

The present disclosure relates to a novel oxygen-generating biodegradable surgical mesh, and to methods of making and using the novel oxygen-generating biodegradable surgical mesh.

In one embodiment, the present disclosure provides a surgical mesh, wherein the surgical mesh has a flexible basic structure and comprises a plurality of pores, wherein the surgical mesh has a first face and a second opposite face, wherein the surgical mesh is made of a substantially homogeneous material comprising a biodegradable polymeric material and an oxygen-generating material.

DETAILED DESCRIPTION

Figure 1:
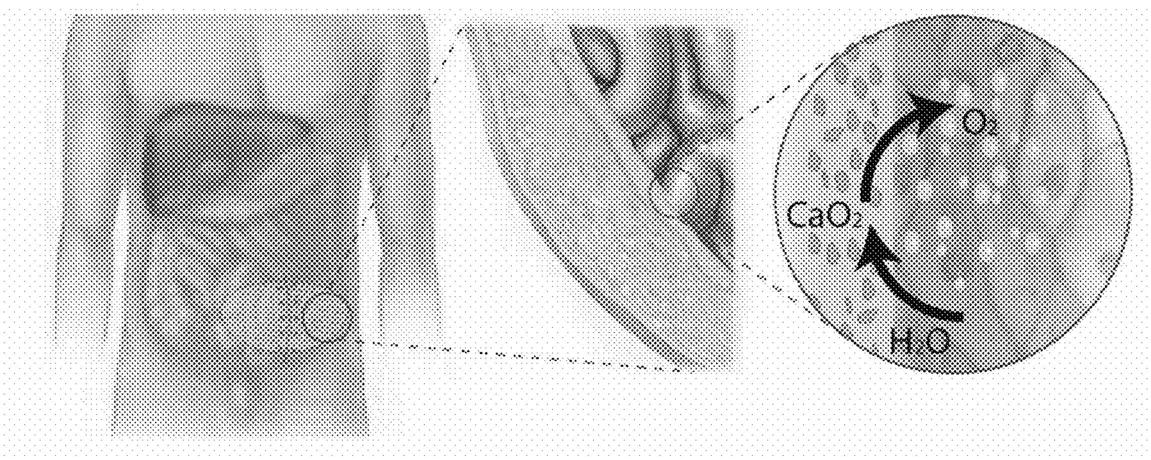
FIG. 1 illustrates the potential application of the proposed biodegradable and oxygen generating surgical mesh, CPO particles are identified as black dots in the zoomed in portion of mesh.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

The present disclosure provides a cost effective, scalable, and solvent-free process of manufacturing polycaprolactone (PCL)-calcium peroxide (CPO) resorbable thin film as an alternative to surgical mesh with ability to provide effective mechanical strength and sustained release of oxygen for limiting hypoxia-induced necrosis within the implanted area (FIG. 1). The utilized PCL polymer matrix is advantageous because of its low melting temperature (~55° C., depending on the molecular weight), extended time required to fully degrade, biocompatibility, and lower cost as compared to biological polymers. Previous studies have shown PCL to last for more than two years as an implant in the body which is ideal for the required duration of service in many implanted surgical meshes. Furthermore, the current disclosure has utilized manufacturing methods take advantage of series of scalable manufacturing methods including hot melt mixing, compression molding, and laser micro machining. The demonstrated fabrication procedure can be readily adapted to roll-to-roll fabrication processes for commercialization and mass production.

Materials and Methods

PCL-CPO Melt Mixing

Figure 2:
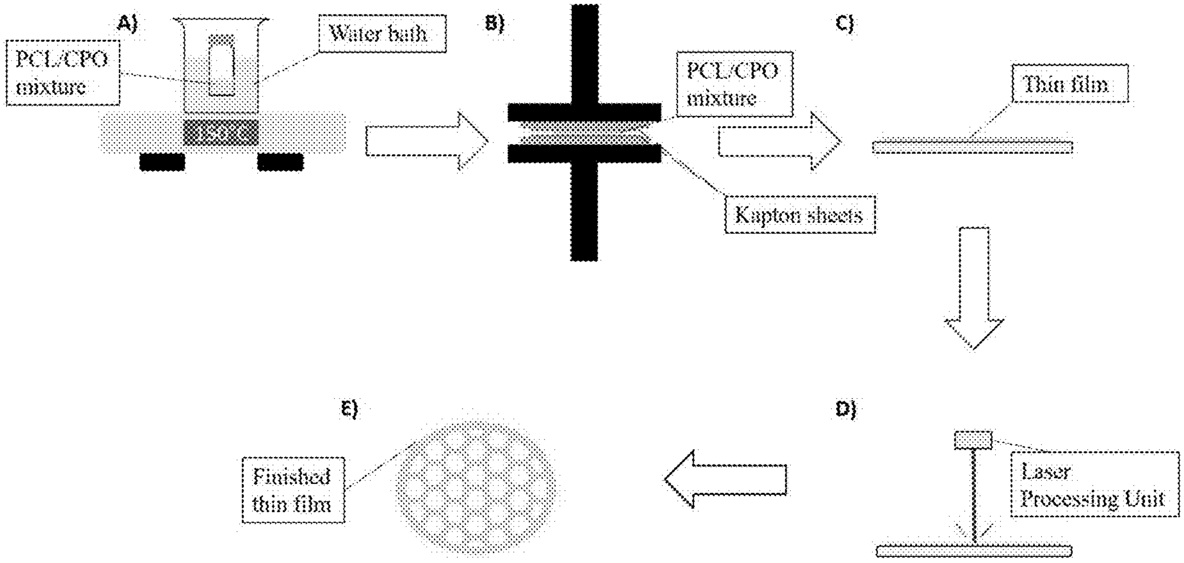
FIG. 2 illustrates the fabrication process for CPO-PCL mesh. (A) PCL pellets are hot melt mixed with CPO. (B) This mixture is compression molded into a 150 μm thick film (C), then laser processed (D) into the final thin film mesh. (E) Schematic representation of mesh with honeycomb pores.

It is necessary to have a uniform mixture before compression molding in order to have a consistent concentration of CPO throughout the film after molding. Therefore, PCL and CPO were melt mixed at different weight ratios (0, 1, 5, and 15 wt %) in a beaker uniformly heated by a water bath on a hot plate set at 90° C. For faster melting, the PCL pellets (Mw 65,000, Sigma Aldrich) were gradually added in 1 gram at a time, until the final amount of PCL was melted. Next, under continuous stirring, proportional quantities CPO was added to the melted PCL to obtain the desired loading concentrations. The mixtures were stirred continuously for about 30 min to achieve uniformity. Finally, the PCL-CPO melt mixture was transferred onto a silicone sheet to solidify and cool down to room temperature. All solid polymer mixtures were stored under nitrogen gas before the compression molding process (FIG. 2, Step A).

Compression Molding

Approximately 2 grams of the PCL-CPO mixture was placed in between two Kapton sheets. The polymer mixture was then flattened between 2 metal sheets using a compression molding machine (Carver Hydraulic Unit Model #3925). Prior to applying pressure, the mixture was heated at 82.2° C. for 20 minutes. 11 tons of pressure was then applied for 5 minutes. The Kapton sheets were removed from the compression molder and allowed to cool for another five minutes before carefully removing the thin film from the Kapton sheets. All thin films were stored in a nitrogen box before further laser processing and other characterization (FIG. 2, Step B and Step C).

Laser Micromachining

Desired surgical meshes with different dimensions of hexagonal shaped pores were generated using CorelDraw (Corel Corporation) cut in to the PCL-CPO thin films using a $CO_2$ laser cutting and engraving system (PLS6MW, Universal Lasers, Inc., Scottsdale, AZ). For clean cuts the laser source power and scanning speed was set to 2 m/s and 60 W, respectively. FIG. 2, Step D and Step E).

Figure 3:
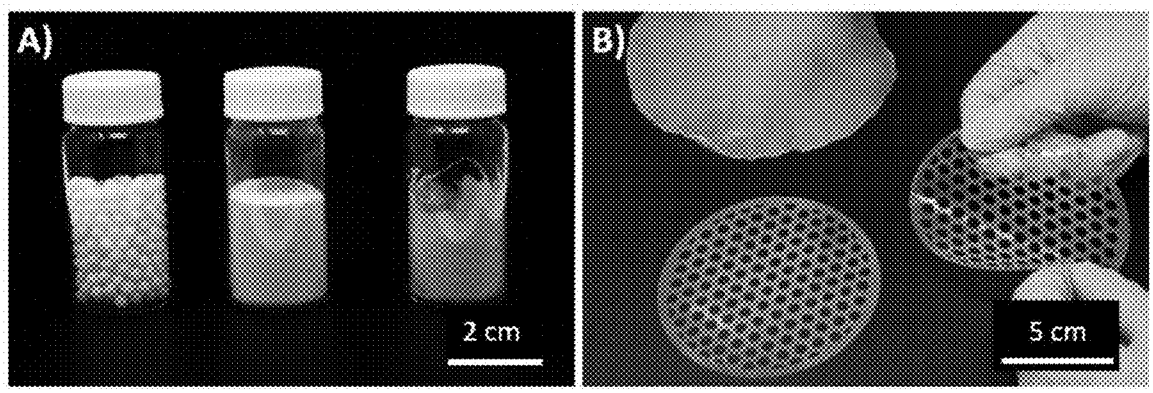
FIG. 3 illustrates (A) From left to right: PCL pellets, CPO powder and cooled mixture of PCL and CPO. (B) Thin film PCL-CPO (CPO 5 wt %, top left), and two pieces of flexible laser cut meshes. The mesh on the right shows the flexibility of the mesh.

Meshes with three different hexagonal pore dimensions were laser cut including: 2.5 mm height×2.5 mm width, 5 mm height×5 mm width, and 10 mm height×10 mm width. The hexagons for each respective pore size were evenly spaced 3 mm apart from each other. FIG. 3 illustrates the complete fabrication process for the functional PCL and CPO mesh.

Oxygen Generation Measurements

Oxygen generation capabilities of the composite meshes with different ratios of CPO filling content were determined by submerging laser cut 1 cm in diameter circular thin film mesh samples into a 50 mL conical tube (Corning, USA) containing 1.5 mL of phosphate buffered saline. During entire measurement the tubes were sealed from the atmospheric environment to minimize the escape of generated oxygen from the container. The levels of dissolved oxygen in the container were measured by a RedEye Oxygen Sensor patch (Lightwind, USA) placed inside the container. The patch contains immobilized ruthenium complex dyes that change in fluorescence properties in the presence of oxygen. The changes in fluorescence properties of the patch were measured by a bifurcated optical probe (RE-BIFBORO-2) pointed at the part of the container where the RedEye patch was located. This eliminates the need to open the container for the oxygen measurements.

Tensile Testing

It is important to understand the mechanical properties of the developed mesh because there are strength requirements for mesh to provide adequate structural support in the body. In order to understand the mechanical properties of the mesh, we performed tensile testing upon the mesh according to the following parameters. Rectangular samples (3 mm×35 mm) were fabricated using a laser cutter equipped with a $CO_2$ laser with same setting as described before. The samples were tested using an ADMET Mtestquattro universal tensile machine at room temperature with a jog rate of 3 mm/min.

It is also important to understand the mechanical properties of the mesh after exposure to the conditions of the body. Therefore, tensile testing was also performed upon samples that had been submerged in phosphate buffered saline (PBS) for 24 hours under the same parameters as described previously.

Mesh Tensile Testing

Tensile testing was also performed upon samples that were processed into mesh patterns in order to both determine mechanical properties of the mesh and acquire data to build a model for the material. The tensile testing was done on a stretching machine capable of applying force unilaterally upon both ends of a sample. A jog rate of 3 mm/min was used for the tests.

Differential Scanning Calorimetry (DSC) and Thermogravimetric Analysis (TGA)

In addition to mechanical properties, it is also useful to understand the thermal properties of a material. It is important to ensure the materials being implanted in the body will neither degrade nor deform due to the temperatures of the environment. DSC and TGA measure the glass transition temperature, melting temperature and degradation temperature.

About 5 mg of each sample was used for TGA. The samples were analyzed using a TG 209 F3 Tarsus. CPO and the 15 wt % thin film were heated to a max temperature of 900° C., while pure PCL was heated to a max temperature of 800° C. All samples were heated at a rate of 20° C./min under a flow of nitrogen gas.

For DSC, 2-10 mg of each sample was analyzed using a DSC 214 Polyma. The samples were all heated to a temperature of 200° C. at a rate of 20° C./min, cooled to 25° C., then heated again to 200° C., all under a flow of nitrogen gas. The purpose of the first heating of the samples was to remove any impurities from the samples.

Scanning Electron Microscopy (SEM)

In order to visually confirm the presence of CPO and inspect the morphology, SEM was performed upon the thin film samples. The samples were all sputter coated (SPI-Module, SPI Supplies, West Chester, PA) with Au—Pd for 3 minutes at 1-minute intervals. Scanning electron microscopy (field-emission SEM, Hitachi S-4800) operated at 20.0 kV at 100× and 1000× magnification was used to assess the morphology and microstructures of the polymer composite films before and after exposure to liquid environment.

Cell Culture Biocompatibility with Human Mammary Cells

It is essential to ensure biocompatibility with the thin film because it will be implanted inside the body. Therefore, human mammary stromal fibroblasts, HMS-32 hTERT cells (between passages 4 and 8) were used to perform cell culture assays with thin films of different concentrations. HMS 32 cells were cultured in Dulbecco modified Eagle medium (DMEM)/F12 medium (Invitrogen Inc., Carlsbad, CA) supplemented with additives, insulin (250 ng/ml; Sigma-Aldrich), hydrocortisone (500 μg/ml; BD Biosciences, San Jose, CA), sodium selenite (2.6 ng/ml; BD Biosciences), transferrin (10 ug/mL; Sigma-Aldrich), transforming growth factor beta 1 (TGFβ1) (30 pg/ml; Thermofisher, Waltham MA), and fibroblast growth factor (FGF)) 5 ng/ml (Thermofisher). The cells were plated on 18 mm coverslips (Thermofisher, Waltham MA) with seeding density of 2500 cells/$cm^2$ and placed in a 12-well plate with and without circular PCL-CPO strips (10 mm diameter) of the following concentrations: 0 (control), 5, and 15 wt % CPO. Cells were cultured at 37° C. in a humidified environment with 5% carbon dioxide, and the culture medium was changed every two days. Cells on days 2 and 6 of culture, using caspase-3 staining cell survival and apoptosis, were monitored under different culture conditions.

Hypoxic Cell Culture Viability

In addition to biocompatibility of the thin films, it is important to make sure the thin films support the viability of cells in hypoxic conditions. To accomplish this, HMS-32 cells were cultured on 12 mm glass cover slips (Thermofisher) as described above and placed in 20 mL scintillation vials without (control) and with a strip of 15 wt % CPO thin film. Hypoxic conditions were introduced into the vials by bubbling nitrogen gas into the solution for 15 minutes and sealing the vials thereafter until day 6. The seal was not removed and there was no medium change. Cells were exposed to low $CO_2$ and $O_2$ levels. On day 6, cells on 12 mm cover slips were processed for staining with Caspase-3 to assess cell viability.

Fluorescence Immunostaining

Antibody against Caspase-3 (Cell signaling technologies, Boston, MA, 1:400 dilution) was used for testing the toxicity of the PCL-CPO material at different concentrations and to assess survival in the presence of the film under hypoxic conditions. Cells were fixed with 4% paraformaldehyde (Sigma-Aldrich) and processed for immunostaining as described previously. Cells were stained with Alexaflour @480 conjugated phalloidin (Thermofisher; 1:40 dilution) to stain F-actin (green) in the cytoplasm. Nuclei were counter-stained with DAPI (500 μg/ml). Images were recorded using Q-capture image acquisition software linked to a BXI70 inverted fluorescence microscope (Olympus, Waltham, MA), with 40× objective (NA=0.65).

Results and Discussion

Figure 4:
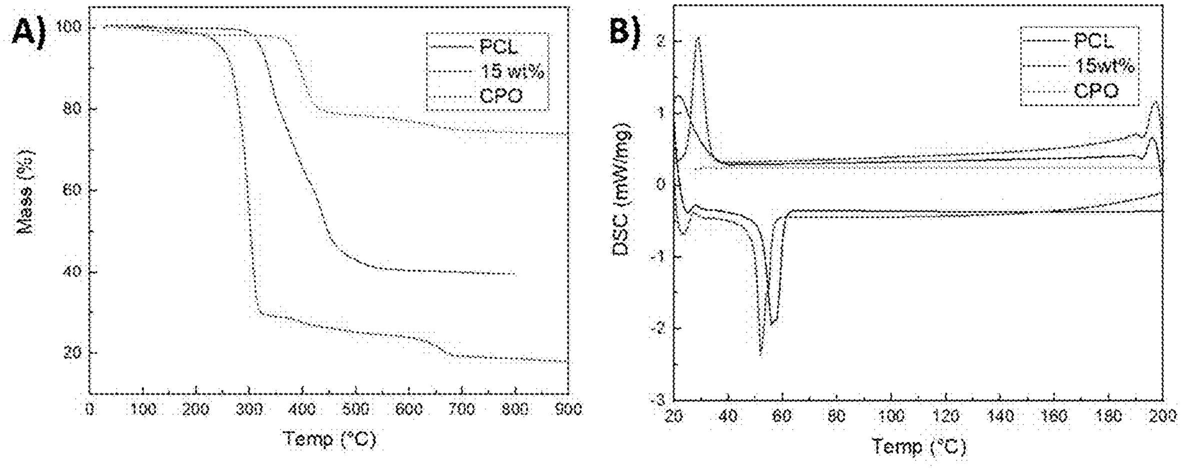
FIG. 4 illustrates thermogravimetric analysis (TGA, 4A) and differential scanning calorimetry (DSC, 4B) of pure PCL, pure CPO, and the 15 wt % CPO thin film.

In order to assess the process viability of the thin film, DSC and TGA were performed first to ensure the temperature required to melt PCL in a water bath would not surpass the degradation temperature of the polymer and the temperature in the body would not cause deformation or degradation of the mesh. As shown in FIG. 4A, the peak decomposition temperatures (339° C., 397° C., and 296° C.) for PCL, CPO and 15 wt % thin film, respectively, are more than 240° C. above the peak melting temperatures of the 15 wt % thin film and pure PCL (51.9° C. and 55.9° C., respectively), shown in FIG. 4B. The temperatures at which the thin film either melt or degrade are far higher than temperatures inside the body. Therefore, there is no risk for the mesh to either deform or degrade due to excessive temperatures. Additionally, because manufacturing temperatures do not exceed, 90° C., there is no risk for degradation during fabrication.

Figure 5:
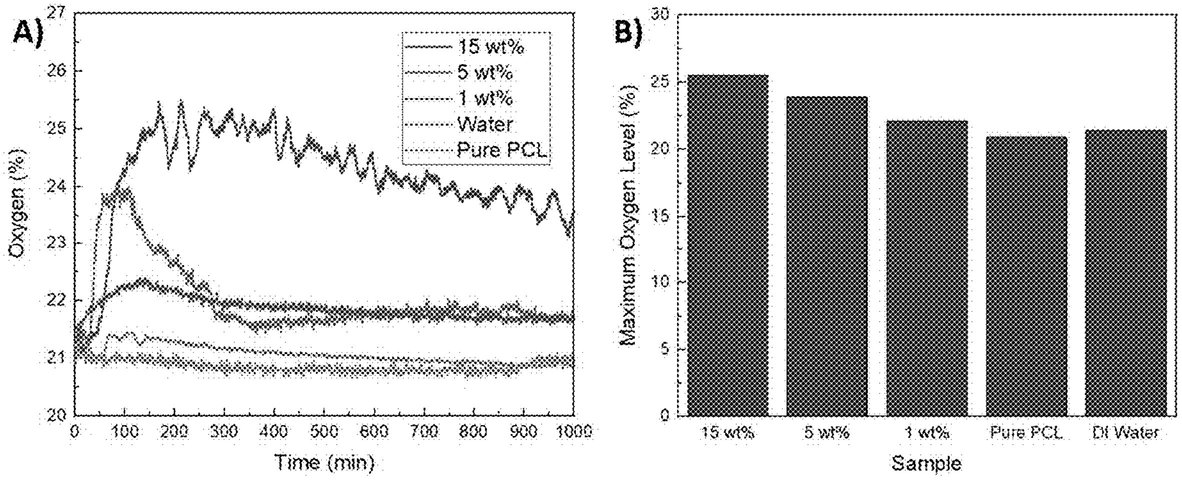
FIG. 5 illustrates oxygen generation measurements of water and all thin film samples over 17 hours. Thin film samples were tested in phosphate buffered saline (PBS). Samples were all kept under nitrogen gas before use. Samples were approximately the same diameter as the conical tube used to contain the experiment.

After confirmation of thermal stability, oxygen generation capacity measurements were performed to quantify the amount of oxygen produced by each concentration of CPO. FIG. 5 shows the results from the oxygen generation experiments. All thin films experienced a short burst of oxygen production immediately when the films were placed in the PBS, presumably from exposed CPO on the surface of the thin film, before a delay of no oxygen production ranging from 18 minutes for 1 wt % to 47 minutes for 15 wt %. As the concentration of CPO increased, the amount of oxygen produced also increased (FIG. 5A). The maximum levels of oxygen produced from the thin films ranged from the 1 wt % CPO thin film with 22.1% oxygen to the 15 wt % CPO thin with 25.5% oxygen (FIG. 5B). After the maximum oxygen levels were reached, there is a decline in concentration of oxygen for all samples containing CPO. We believe the decrease in oxygen levels after reaching the peak levels is a result of the oxygen levels equilibrating in the container. Because the thin film is placed very close to the RedEye sensor, most of the oxygen is generated near the sensor, hence a higher concentration near the sensor. Therefore, the local concentration of oxygen near the sticker must be higher than the surrounding liquid until the oxygen diffuses equally throughout the apparatus.

In thin films with lower amounts of CPO (1 and 5 wt % CPO), a plateau is observed because there is less CPO to react in these thin films, and for that reason they produce less oxygen than the 15 wt % thin film. The lower oxygen output from the 1 and 5 wt % thin films would therefore equilibrate sooner than the 15 wt % thin film.

Figure 6:
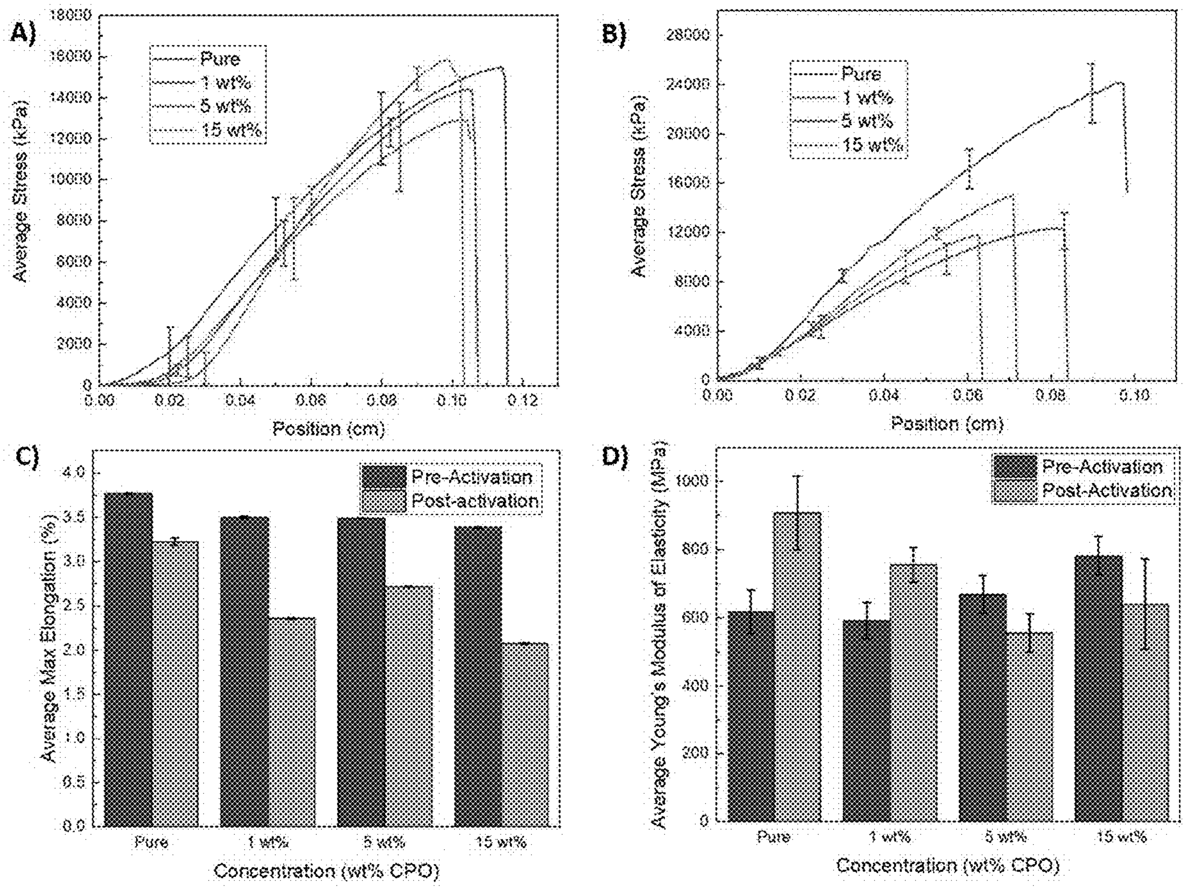
FIG. 6 illustrates stress vs. strain curve of PCL-CPO polymer with different loading concentrations of CPO (A) pre-activation and (B) post-activation in PBS for 24 h. (C) average Young's modulus of elasticity for samples pre-activation and post-activation as a function of CPO loading concentrations. (D) maximum elongation for pre-activation and post-activation in PBS for 24 h.

FIG. 6A shows the tensile properties of the thin films with varying amounts of CPO prior to being placed in a wet environment. The results from the experiment show the tensile strength of the thin films increasing as the concentration of CPO in the thin films increases, from 12900 kPa (±2170) for the 1 wt % thin film to 14500 kPa (±695) for the 5 wt % thin film to 15900 kPa (±546) for the 15 wt % thin film. The exception to this trend is the pure PCL thin film which has a tensile strength of 15500 kPa (±1770).

FIG. 6B shows the tensile properties of the thin films after being soaked in PBS for 24 hours. The thin films with CPO decreased in tensile strength as the concentration of CPO increased, from 14900 kPa (±449) in the 1 wt % thin film to 12300 kPa (±1490) in the 5 wt % thin film to 11800 kPa (±1330) in the 15 wt % thin film. However, the pure PCL thin film exhibited a much higher tensile strength than any of the other films at 24200 kPa (±2410). The surface porosity created as the CPO initially present on the surface reacts most likely creates weaker areas in the thin films that lessens the tensile strength of the thin films with CPO. However, PCL thin film without CPO do not experience the decrease in tensile strength.

FIG. 6C illustrates the differences in the amount of elongation the thin films can endure pre-activation and post-activation. The maximum elongation decreases as the amount of CPO in the thin films increase for both pre-activation and post-activation. This decrease in elongation is also due to the surface porosity created by CPO reacting with PBS, which causes a more brittle material.

The Young's modulus of Elasticity, shown in FIG. 6D, shows a large difference between samples before and after activation (before and after immersion, respectively). For the 0 and 1 wt % CPO samples before immersion in PBS, the Young's modulus of elasticity is less than the samples previously immersed in PBS, whereas the opposite is true for the 5 and 15 wt % CPO samples. It appears from FIG. 6D that there is a critical amount of CPO in PCL where the Young's modulus of elasticity is not affected by soaking in PBS for 24 hours because of this observed trend. It is known that water breaks down the polymer chains in PCL, leading to a more brittle material, which explains the behavior of the pure PCL samples. For the samples with larger amounts of CPO, the higher density of pores created on the surface of the material from CPO reacting with water must compromise the structural integrity of the material more than the water makes the polymer matrix brittle, resulting in a decrease in Young's modulus for samples post-activation. This critical point must be somewhere in between 1-5 wt % CPO.

Figure 7:
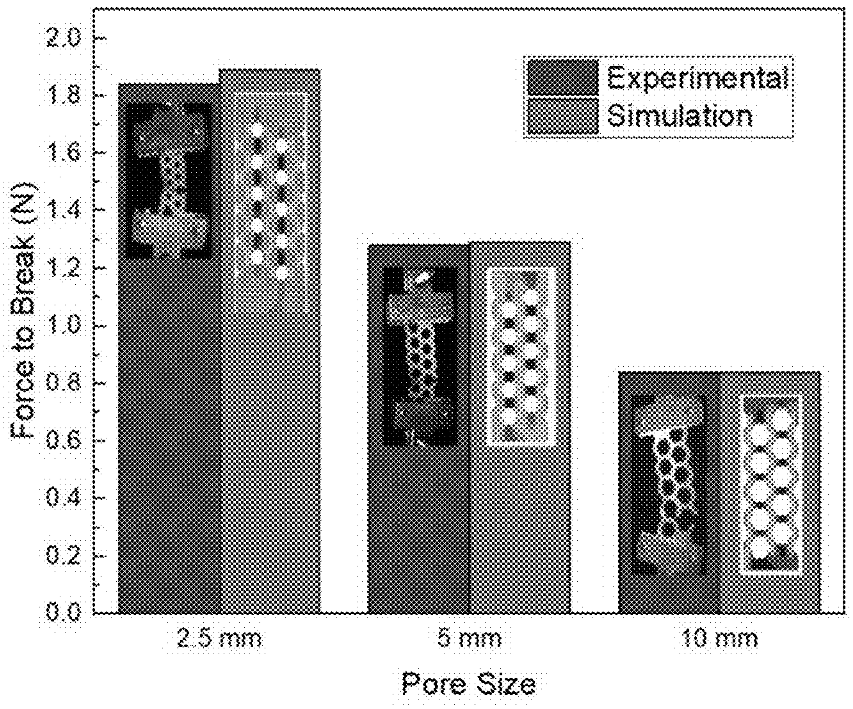
FIG. 7 illustrates Force versus displacement for different honeycomb structures with inlaid pictures of each sample in each respective trial. Pore size is the dimensions of the hexagon (i.e. 5 mm pore size corresponds to mesh comprised of hexagonal holes with heights and widths of 5 mm). The separation between pores for all three sizes stayed consistent at 3 mm.

FIG. 7 shows the force required to break laser machined meshes with different pore sizes onto thin films PCL with 15 wt % CPO filler. These results are supported by the simulations done in Abaqus. For each pore size (2.5 mm, 5 mm and 10 mm), failure was observed at the point where maximum von Mises stress occurred. Experimentally, the sample undergoes the same amount of elongation as in simulation. As can be seen from the images taken from simulation, maximum stress occurred mostly at the edges of the mesh due to the stress concentration at the corners of the sample. These results are supported by the simulations done in Abaqus shown in FIG. 7. The experimental results are all very close or equal to the simulation results, thus indicating an accurate model.

Figure 8:
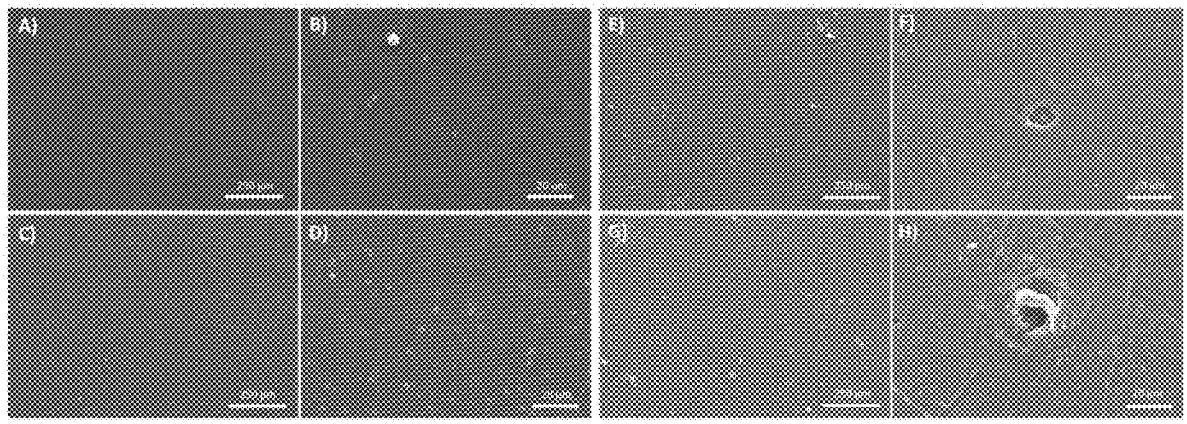
FIG. 8 illustrates Scanning electron microscopy (SEM) images of thin film samples at different concentrations and multiple magnifications both before and after immersion in PBS for 24 hours. Thin films with two concentrations of CPO were imaged, specifically the 5 wt % film at (A) 100× magnification and (B) 1000× magnification, the 15 wt % film before immersion at (C) 100× magnification and (D) 1000× magnification. The 5 wt % film was imaged after immersion at (E) 100× magnification and at (F) 1000× magnification. The 15 wt % film was imaged after immersion at (G) 100× magnification and at (H) 1000× magnification.

SEM images were conducted to visually confirm the uniformity of the CPO particles distribution in the thin film composite. FIG. 8A shows the 5 wt % CPO thin film at 100× magnification. FIG. 8B shows the same film at 1000× magnification. The CPO particles can be identified as spots of white and lighter shades of grey. Although the CPO in the 5 wt % thin film is distributed evenly, there is not a high concentration (FIG. 8B). FIG. 8C and FIG. 8D show the 15 wt % thin film at 100× and 1000× magnification, respectively. It can be seen clearly in FIG. 8D that the CPO particles are still distributed evenly but in a higher concentration than in the 5 wt % thin film. Additionally, it is evident in FIG. 8B and FIG. 8D that some of the CPO particles are embedded beneath the surface because some of the CPO spots are light grey rather than white, signifying their presence just below the surface of the PCL. This partial encapsulation of CPO particles allows a more sustained release of oxygen as the PCL breaks down in the body rather than a burst release if all the CPO was on the surface.

SEM images were also taken of the composite films after being immersed in PBS to assess its change in structural properties. FIG. 8E and FIG. 8F show the 5 wt % thin film after being soaked in PBS for 24 hours. FIG. 8F shows the formation of a hole in the surface of the polymer film where a particle of CPO was before reacting with PBS. FIG. 8G and FIG. 8H show the 15 wt % film after being soaked in PBS for 24 hours. Higher magnification images confirm that the increase in CPO filler content leaved behind more holes in the surface of the polymer film after immersion into PBS solution, FIG. 8H.

Figure 9:
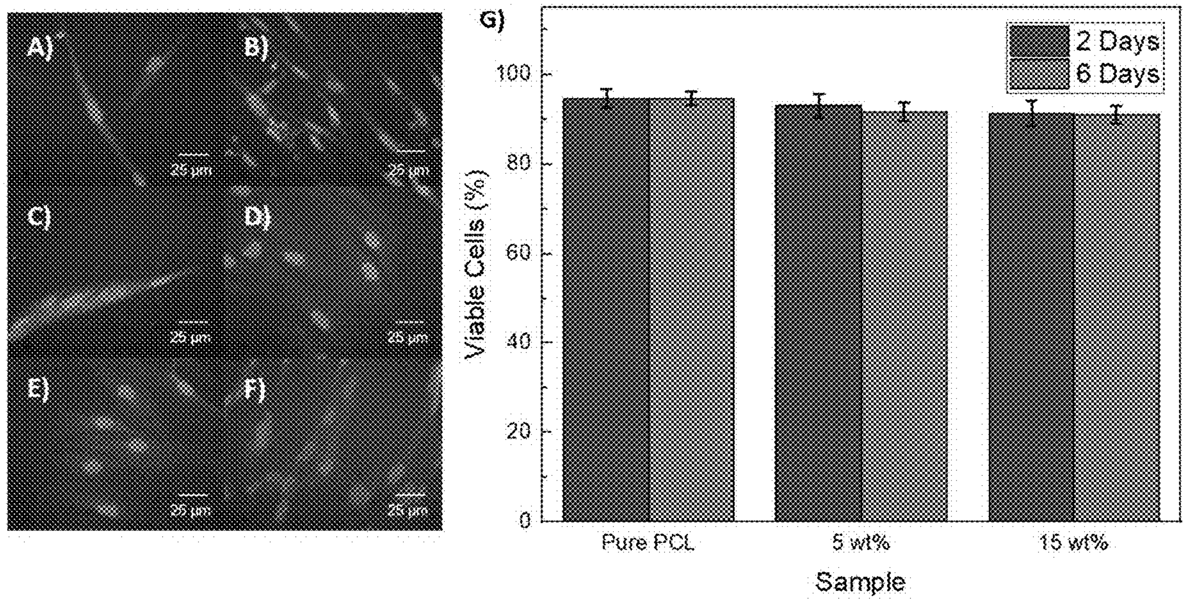
FIG. 9 illustrates Cell cultures fixed with 4% formaldehyde and permeabilized with 0.1% Triton X-100 after exposure to different concentrations of CPO mesh at both time periods. (A) 0 wt % at 2 days; (B) 0 wt % at 6 days; (C) 5 wt % at 2 days; (D) 5 wt % at 6 days; (E) 15 wt % at 2 days; (F) 15 wt % at 6 days. (G) shows the percent viable cells for the different concentrations at both time points. N=300 in three biological replicates. Magnification 40×; Objective N/A: 0.65.
Figure 10:
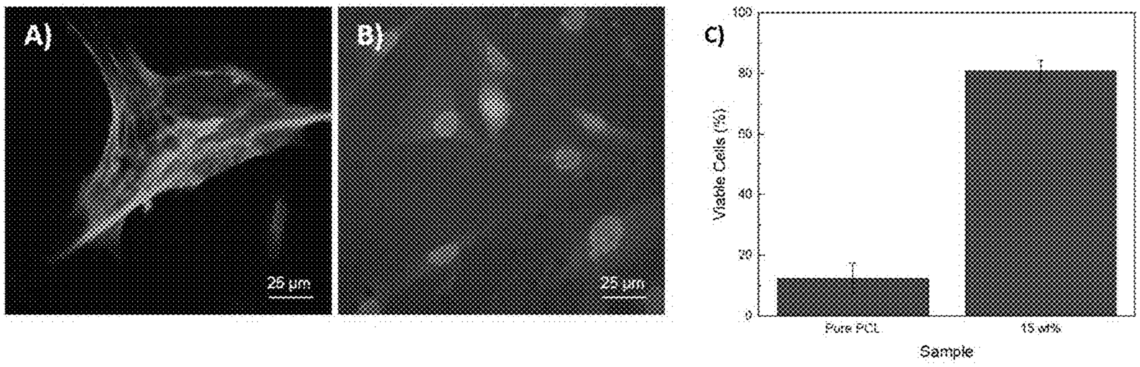
FIG. 10 illustrates Immunofluorescence images of HMS 32 cells show phalloidin staining (green) to show F-actin distribution in the cytoplasm and DAPI to stain nuclei (blue) on (A) control (no film) and (B) 15 wt % CPO in vial on day 6 of cell culture. (C) Bar graphs with percentage of viable cells stained positive for caspase-3 on day 6 of culture in control and 15 wt % CPO vials. n=150 in three technical replicates. Magnification 40×; Objective N/A: 0.65. *$p<0.05$; *$p<0.01$: *$p<0.001$.

To assess the biocompatibility of the thin films with human cells, different concentrations of thin films were cultured with HMS-32 cells. Based on caspase-3 based cell viability measurement on the HMS-32 cells, the PCL-CPO is biocompatible even at 15 wt %, the highest concentration tested. The cell survival did not change significantly as compared to the control (FIG. 9G). In this case we have used an inverted fluorescence microscope to determine the cell viability and subsequent imaging. Based on caspase staining, 90-92% cells were viable when cultured on any of the substrate materials (FIG. 9G). There was no significant difference in percentage of viable cells on day 2 which is an earlier stage of assessing the compatibility and on day 6 by which fibroblasts are expected to differentiate in the presence of growth additives provided (FIG. 9A). There was no change in the phenotype of the cells (FIG. 9A-FIG. 9F). These results show that the presence of increasing amounts of CPO do not greatly impact the viability of cells. Because of the viability results, we chose to focus on the 15 wt % thin film, as it produces the most oxygen of all the thin films.

Although the films were determined to be biocompatible with human cells, it was still necessary to show the capacity of the films to aid in the survival of cells in hypoxic conditions. For this test, PCL film with 15 wt % CPO fillers were introduced into sealed cell culture vial in hypoxic conditions. To assess the oxygen-generating the functionality on cell survival, the amount of live or dead cells was visualized and quantified after day 6, FIG. 9A-FIG. 9B. The control cell culture group in hypoxia condition underwent significant amounts of cell death with only 15% surviving cells. However, the PCL film with 15 wt % CPO demonstrated cell survival rates of up to 80%. Although this number is significantly lower than usual survival rate in HMS-32 cells cultured under regular conditions, it is expected that there is more cell death in the vials with low $O_2$ and $CO_2$. Because of the increased survival rates for cells in hypoxic conditions exposed to the 15 wt % thin film, we believe PCL-CPO thin film composite meshes show great promise for use in surgical mesh applications.

Oxygen-generating biodegradable surgical mesh were fabricated by incorporating varying concentrations of CPO in PCL polymer matrix. The use of scalable manufacturing methods, including hot melt mixing, compression molding, and laser processing enabled to greatly reduce the manufacturing complexly and production of the composite mesh. The tensile strength of the composites with CPO filler of up to 15 wt % was found to be provide enough strength for a wide range of hernioplasties application with the require a tensile strength of 24 kPa. The rate of oxygen-generation of the polymer composite upon exposure to liquid confirmed a consistent increase with higher CPO filler content. Cytotoxicity studies with human mammary stromal fibroblasts confirmed the biocompatibility of a polymer composite with different CPO concentrations of up to 15 wt %. In vitro cell viability studies in hypoxic conditions confirmed the ability of the PCL composite with 15 wt % CPO filler to effectively reduce hypoxia-induced cell death by limiting the necrosis over 6 days of culture. The demonstrated PCL-CPO composite shows great potential to replace or supplement currently available surgical meshes. Future work should investigate long-term impacts that the thin film meshes may have on the body.

In one embodiment, the present disclosure provides a surgical mesh, wherein the surgical mesh has a flexible basic structure and comprises a plurality of pores, wherein the surgical mesh has a first face and a second opposite face, wherein the surgical mesh is made of a substantially homogeneous material comprising a biodegradable polymeric material and an oxygen-generating material.

In one embodiment regarding the surgical mesh of this disclosure, wherein the biodegradable polymeric material may be but is not limited to poly(lactic-co-glycolic acid) (PLGA), thermoplastic polyurethane (TPU), or polycaprolactone (PCL). In one aspect, the biodegradable polymeric material is polycaprolactone (PCL).

In one embodiment regarding the surgical mesh of this disclosure, wherein oxygen-generating material may be but is not limited to sodium percarbonate, calcium peroxide, magnesium peroxide, or any combination thereof. In one aspect, the oxygen-generating material is calcium peroxide.

In one embodiment regarding the surgical mesh of this disclosure, wherein the biodegradable polymeric material comprises polycaprolactone, wherein the oxygen-generating material comprises calcium peroxide.

In one embodiment regarding the surgical mesh of this disclosure, wherein the polycaprolactone has a weight percentage of 85% to 98% of the total weight of the surgical mesh, wherein the calcium peroxide has a weight percentage of 2% to 15% of the total weight of the surgical mesh.

In one embodiment regarding the surgical mesh of this disclosure, wherein the plurality of pores have uniform size and shape to provide consistent oxygen releasing rate.

In one embodiment regarding the surgical mesh of this disclosure, wherein the surgical mesh has a thickness of 100-500 μm, 100-400 μm, 100-300 μm, 100-200 μm, 100-150 μm.

In one embodiment regarding the surgical mesh of this disclosure, wherein the surgical mesh is biocompatible and has over 80% of cell survival rate in hypoxic condition.

In one embodiment, the present disclosure provides a method of preparing the surgical mesh of the present disclosure, wherein the method comprises:

providing a biodegradable polymeric material and melting the biodegradable polymeric material;

providing an oxygen generating material and adding the oxygen generating material to the melted biodegradable polymeric to form a substantially homogenous melt mixture;

cooling the substantially homogenous melt mixture to provide a substantially homogenous solid mixture;

providing an amount of the substantially homogenous solid mixture and heating to an elevated temperature and then compression molding the substantially homogenous solid mixture to a sheet with a thickness of 100-500 μm; and laser micromachining the sheet to generate a plurality of pores.

In one embodiment regarding the method of preparing the surgical mesh of the present disclosure, wherein the biodegradable polymeric material comprises polycaprolactone, wherein the oxygen-generating material comprises calcium peroxide.

In one embodiment, the present disclosure provides a method of using the surgical mesh of the present disclosure, wherein the method comprises:

providing the surgical mesh of claim 1 to a patient during a surgery process; and applying the surgical mesh to a surgical site of the patient to provide structural support to the surgical site, and to provide an oxygen source.

In one embodiment regarding the method of using the surgical mesh of the present disclosure, wherein the method is used to control bacteria prefiltration.

In one embodiment regarding the method of using the surgical mesh of the present disclosure, wherein the biodegradable polymeric material comprises polycaprolactone, wherein the oxygen-generating material comprises calcium peroxide.

Those skilled in the art will recognize that numerous modifications can be made to the specific implementations described above. The implementations should not be limited to the particular limitations described. Other implementations may be possible.

We claim:

1. A solvent-free method of preparing a mesh material, wherein the method comprises:

melting a biodegradable polymeric material;

adding an oxygen-generating material to the melted biodegradable polymeric to form a substantially homogenous melt mixture;

cooling the substantially homogenous melt mixture to provide a substantially homogenous solid mixture;

heating an amount of the substantially homogenous solid mixture to an elevated temperature;

compression molding the amount of the heated substantially homogeneous solid mixture to a sheet; and laser micromachining the sheet to generate a plurality of pores, thus providing the mesh material.

2. The method of claim 1, wherein the biodegradable polymeric material comprises at least one of poly(lactic-co-glycolic acid) (PLGA), thermoplastic polyurethane (TPU), and polycaprolactone (PCL).

3. The method of claim 2, wherein the biodegradable polymeric material is PCL.

4. The method of claim 3, wherein the oxygen-generating material comprises at least one of sodium percarbonate, calcium peroxide, and magnesium peroxide.

5. The method of claim 3, wherein the oxygen-generating material comprises calcium peroxide.

6. The method of claim 5, wherein the PCL has a weight percentage of 85% to 98% of the total weight of the surgical mesh, and wherein the calcium peroxide has a weight percentage of 2% to 15% of the total weight of the surgical mesh.

7. The method of claim 6, wherein the calcium peroxide has a weight percentage of 5% to 15% of the total weight of the surgical mesh.

8. The method of claim 1, wherein the plurality of pores have uniform size and shape to provide consistent oxygen releasing rate.

9. The method of claim 7, wherein the plurality of pores have a hexagonal cross-sectional shape.

10. The method of claim 8, wherein each of the plurality of pores are evenly spaced apart.

11. The method of claim 5, further comprising a step of applying the mesh material to a surgical site of a patient.

12. The method of claim 5, wherein the sheet has a thickness of 100-500 μm.

13. The method of claim 12, wherein the sheet has a thickness of 100-300 μm.

14. The method of claim 13, wherein the sheet has a thickness of 100-150 μm.

* * * * *